United States Patent [19]

Dubner et al.

[11] Patent Number: 5,639,928
[45] Date of Patent: Jun. 17, 1997

[54] DEHYDRATION OF 1-PHENYL ETHANOL

[75] Inventors: Walter S. Dubner, Wilmington, Del.; Lawrence M. Candela, Philadelphia, Pa.

[73] Assignee: ARCO Chemical Technology, L.P., Greenville, Del.

[21] Appl. No.: 296,769

[22] Filed: Aug. 26, 1994

Related U.S. Application Data

[63] Continuation-in-part of Ser. No. 29,490, Mar. 11, 1993, abandoned.
[51] Int. Cl.$^6$ ..................................................... C07C 1/20
[52] U.S. Cl. ........................... 585/437; 585/435; 585/469
[58] Field of Search ............................... 585/435, 437, 585/469

[56] References Cited

U.S. PATENT DOCUMENTS

| | | |
|---|---|---|
| 3,351,635 | 11/1967 | Kollar .................................. 260/348.5 |
| 3,442,963 | 5/1969 | Korchak . |
| 3,526,674 | 9/1970 | Becker et al. . |
| 3,658,928 | 4/1972 | Skinner et al. . |
| 4,086,147 | 4/1978 | Watson . |
| 4,185,019 | 1/1980 | Watson et al. ........................ 260/340.7 |
| 4,350,825 | 9/1982 | Huang . |
| 4,628,136 | 12/1986 | Sardina . |
| 5,210,354 | 5/1993 | Dubner et al. ........................ 585/469 |

*Primary Examiner*—Asok Pal
*Assistant Examiner*—Bekir L. Yildirim
*Attorney, Agent, or Firm*—William C. Long

[57] ABSTRACT

The present invention relates to the improved liquid phase dehydration of 1-phenyl ethanol to styrene monomer, the improvement comprising the use of a residue formation inhibiting agent during the liquid phase dehydration.

4 Claims, No Drawings

DEHYDRATION OF 1-PHENYL ETHANOL

RELATED APPLICATION

This application is a continuation-in-part of application Ser. No. 08/029,490 filed Mar. 11, 1993, abandoned.

BACKGROUND OF THE INVENTION

1. Field of the Invention

The present invention relates to an improved process for the liquid phase dehydration of 1-phenyl ethanol to produce styrene monomer. In particular, the invention relates to an improved process whereby the formation of undesirable by-products such as heavy condensation products is substantially reduced by incorporating in the liquid phase dehydration mixture an additive which is effective to reduce by-products make.

2. Description of the Prior Art

The dehydration of 1-phenyl ethanol to produce styrene is an important process which is widely practiced throughout the world. For example, in the Oxirane Process for the production of propylene oxide, 1-phenyl ethanol is a convenient co-product, and this material is advantageously converted to styrene monomer which is, of course, an industrial chemical of enormous commercial importance.

The dehydration of 1-phenyl ethanol is, itself, a well known reaction. For example, the vapor phase dehydration of 1-phenyl ethanol is described in U.S. Pat. No. 3,442,963 as well as in U.S. Pat. No. 3,658,928, and the liquid phase dehydration is described, for example, in U.S. Pat. No. 3,526,674.

From the standpoint of economics and efficiencies of operation, it is advantageous to conduct the 1-phenyl ethanol dehydration in the liquid phase in the presence of appropriate catalysts such as is described in U.S. Pat. No. 3,526,674. A disadvantage of such technologies is that a certain percentage of the feed material is converted to undesirable by-products such as heavy condensation products, and the production of these undesirable products lessens the economics and efficiency of the reaction.

It is desirable to reduce the formation of such by-products, and the present invention is specifically designed to accomplish this objective.

BRIEF DESCRIPTION OF THE INVENTION

In accordance with the present invention, 1-phenyl ethanol is dehydrated in the liquid phase in accordance with generally known techniques to produce styrene monomer, the specific improvement of the invention being that the dehydration is carried out in the presence of an agent which is effective to reduce the formation of undesirable heavy residue by-products which are normally produced during the dehydration reaction.

DETAILED DESCRIPTION

Dehydration conditions of temperature and pressure as well as the various catalysts which are used in practice of the present invention are of the generally known type as illustrated, for example, in U.S. Pat. No. 3,526,674. Such procedures generally involve conducting the liquid phase 1-phenyl ethanol dehydration at temperatures ranging from 180° C. to 330° C., preferably 200° C. to 250° C., and at subatmospheric pressures ranging down to 50 mmHg, preferably 100 mmHg to 300 mmHg, sufficient to maintain the liquid phase while permitting removal of product water and styrene as vapor.

Acidic type catalysts are preferably employed; such catalysts include p-toluene sulfonic acid, oxalic acid, sulfuric acid, high surface area alumina and the like.

The unique feature of the present invention is the provision in the liquid dehydration reaction mixture of an agent which functions to improve the dehydration efficiency and to suppress the formation of undesirable, heavy residue by-products during the dehydration reaction. Through the provision of the said agent, reaction efficiencies are improved, the formation of undesirable by-products is lessened and the overall process economics are substantially improved.

The residue suppressing additive agents employed in practice of the invention are nitro or nitroso substituted aromatics which possess the characteristic that the additives do not significantly enter into alkylation or condensation reactions with other materials in the dehydration reaction zone at the relatively severe conditions of the 1-phenyl ethanol dehydration.

Especially advantageous residue suppressing agents employed in accordance with the invention are nitro and nitroso substituted phenols and benzene sulfonic acids. Such agents have the formula:

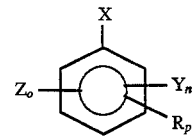

where R is a $C_1$–$C_{10}$ alkyl group, X is —OH or —$SO_3H$, Z is —NO, Y is —$NO_2$, n is 0–2, p is 0–2, p is 0–4, and n+o is 1–2. Specific examples are 4, 6 dinitro-ortho cresol, 2, 6 dinitro-4 methyl phenol, p-nitrosophenol, 2,4 di-nitro benzene sulfonic acid and the like.

Materials used to suppress styrene polymerization under normal conditions such as phenol or alkyl catechols, which do not have the nitro or nitroso substituants, do not produce the improvements of the present invention. In addition, additives used in this invention such as di-nitro benzene sulfonic acid are not known styrene polymerization inhibitors.

In practice of the invention, the residue suppressing agent is used in amount of at least 5 ppm by weight, preferably at least 30 ppm by weight based on the feed to the dehydration up to about 5 wt. %, preferably up to about 1 wt. %, are used.

It should be noted that certain materials previously employed as additives during 1-phenyl ethanol dehydration such as phenol are not effectively employed in the present invention due to the tendency of such materials to react with the aromatic ring during the dehydration, thus aggravating rather than lessening problems of heavy residue formation.

It has been found that significant improvements in heavy residue formation are achieved through practice of the present invention as will be illustrated in the working examples contained herein. It should be pointed out that the conditions encountered in the dehydration of 1-phenyl ethanol are quite severe in that elevated temperatures and acidic catalyst components are involved in the dehydration reaction, and require use of the designated agents for practice of this invention.

The following examples illustrate the invention.

A series of runs was conducted to illustrate the effect of various additives on the formation of heavy residues during the liquid phase dehydration of 1-phenyl ethanol. The feed was comprised of about 80 wt % 1-phenyl ethanol, about 15 wt % acetophenone, and 5 wt % heavier materials. Dehydration conditions included a temperature of 210° C., pressure of 200mmHg absolute, the use of p-toluene sulfonic acid dehydration catalyst in amount of about 95 ppm by weight of the feed. The following table shows the selectivity of the dehydration reaction to styrene and heavy residue (HB) using the designated additives in the indicated weight percentages:

TABLE 1

| Run | Additive | Wt % on Feed | Selectivity % | |
|---|---|---|---|---|
| | | | Styrene | Heavy Residue |
| 1 | None | — | 98 | 1.7 |
| 2 | 4,6 dinitro 2-methyl phenol* | 0.005 | 99+ | 1.2 |
| 3 | Phenol | 0.4 | 97 | 2.6 |
| 4 | p-nitrosophenol | 0.025 | 99+ | 1.2 |
| 5 | 2-ethyl phenol | 0.4 | 97.5 | 2.2 |
| 6 | 2,6 dinitro-4-methyl phenol | 0.005 | 99+ | 1.2 |
| 7 | 2,6 di-t-butyl-4-methyl phenol | 0.010 | 97.5 | 2.0 |
| 8 | Ralox 46** | 0.050 | 98 | 1.7 |
| 9 | 2,4 dinitro benzene sulfonic acid | 0.005 | 99+ | 1.2 |

*also referred to as 4,6 dinitro ortho cresol
**(2,2'-methylene-bis-[4-methyl 6-t-butyl phenol])

Runs 1, 3, 5, 7 and 8 are comparative. Run 1 shows the heavy residue formation where no additive was employed. Runs 2, 4, 6 and 9 show the improved results achieved through practice of the invention. Run 3 shows the deleterious effects of the use of phenol; Run 5 shows the deleterious effects of the use of ethyl phenol, Run 7 shows the deleterious effects of the use of alkyl substituted phenol with no nitro or nitroso group as does Run 8.

We claim:

1. A process for the production of styrene monomer wherein 1-phenyl ethanol is catalytically dehydrated in the liquid phase at elevated temperatures in the range 180° C. to 330° C. to form styrene monomer, the improvement which comprises incorporating in the dehydration reaction mixture a residue formation inhibiting amount of nitro substituted phenol or nitro substituted sulfonic acid additive effective to suppress residue formation.

2. The method of claim 1 wherein said additive is 4,6-di-nitro-ortho-cresol.

3. The method of claim 1 wherein said additive is 2,6 dinitro-4-methyl phenol.

4. The method of claim 1 wherein said additive is 2,4 dinitro benzene sulfonic acid.

\* \* \* \* \*